United States Patent [19]

Walz

[11] Patent Number: 5,540,702

[45] Date of Patent: Jul. 30, 1996

[54] STONE CRUSHING DEVICE

[76] Inventor: Volker Walz, Walddorfer Str. 40, D-72229, Rohrdorf, Germany

[21] Appl. No.: 233,593

[22] Filed: Apr. 25, 1994

[30] Foreign Application Priority Data

Apr. 27, 1993 [DE] Germany .......................... 43 13 768.7

[51] Int. Cl.$^6$ .................................................. A61B 17/22
[52] U.S. Cl. .................................................. 606/128
[58] Field of Search .................................... 606/127, 128, 606/1

[56] References Cited

U.S. PATENT DOCUMENTS

| | | | |
|---|---|---|---|
| 4,474,180 | 10/1984 | Angulo | 606/128 |
| 4,605,003 | 8/1986 | Oinuma et al. | 606/128 |
| 5,160,336 | 11/1992 | Favre | 606/128 |
| 5,243,997 | 9/1993 | Uflacker et al. | 604/22 |

FOREIGN PATENT DOCUMENTS

| | | |
|---|---|---|
| 0317507 | 4/1992 | European Pat. Off. . |
| 2724324 | 8/1978 | Germany . |

*Primary Examiner*—Gary Jackson
*Assistant Examiner*—Glenn Dawson

[57] ABSTRACT

A shock wave lithotrite has a soft iron mass body (33), which is accelerated by the magnetic field produced by a coil (19) and, on impact against a shock receiver (26), abruptly transmits as a shock impulse the kinetic energy thereby accumulated. The shock impulse is transmitted by the shock receiver (26) to an impulse conducting wire (13), passes through the latter in the form of a shock wave propagated between the molecules and passes out at the other end of the wire. The coil (19) can be connected to one of the usual high-voltage pulse generators (11) used for electrohydraulic lithotrites.

12 Claims, 1 Drawing Sheet

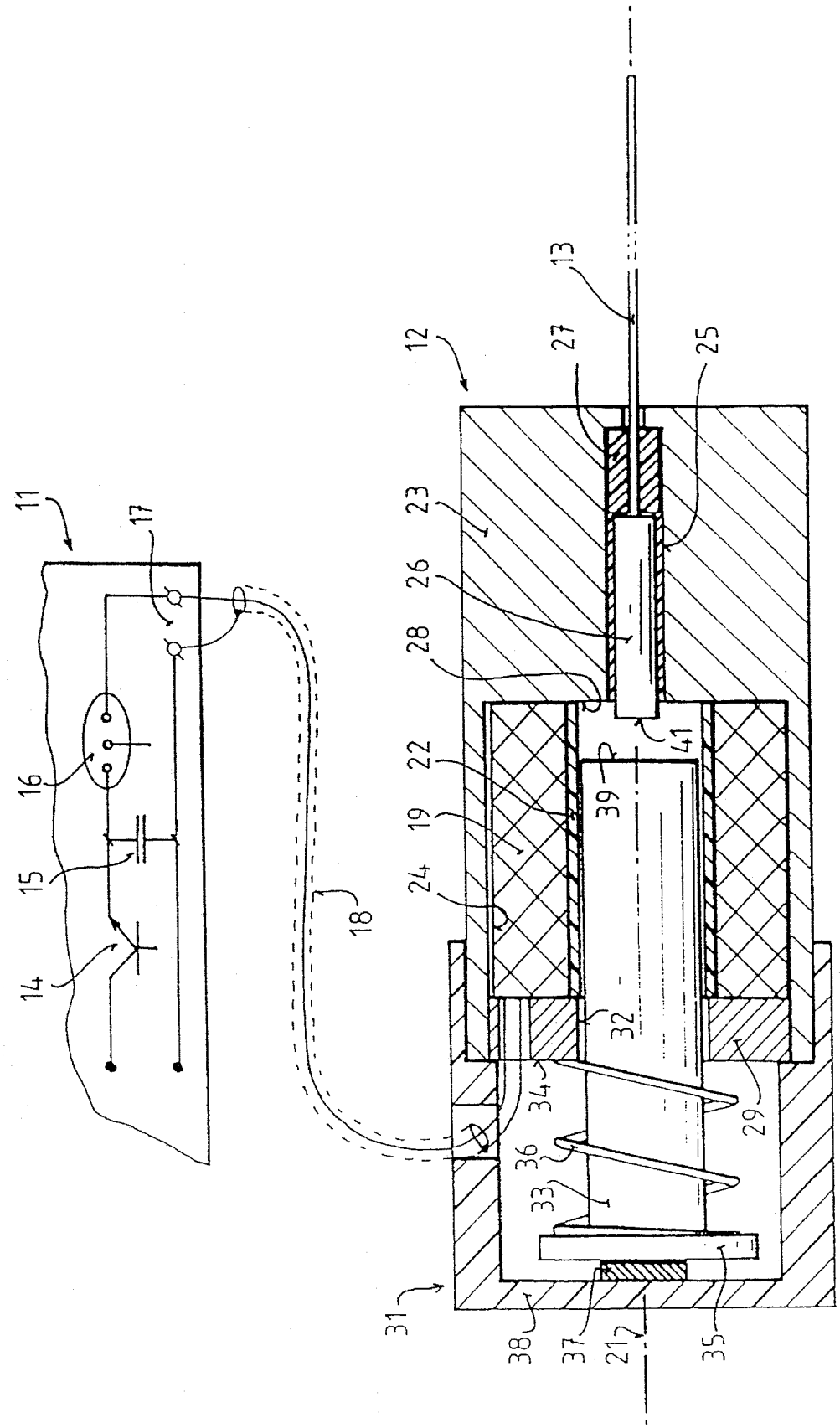

STONE CRUSHING DEVICE

The invention relates to a stone crushing device for medical purposes in accordance with the preamble of claim 1.

A known device of this kind in the form of a shock wave lithotrite is described in EP O 317 507 B1. The principle consists in transmitting a kinetic shock as a wave through a stiff but sufficiently flexible wire to the point of application, the shock energy being produced by guiding a projectile-like mass body as if in a blowgun and shooting it by compressed air against the other end of the wire. The kinetic energy accumulated through the accelerated movement of the mass body is transmitted abruptly when it reaches the wire, passes through the latter as a shock wave and appears equally abruptly at the opposite end, while the wire itself does not make a longitudinal movement. Gallstones, kidney stones and the like can be blasted in this manner.

A disadvantage of this device is the expensive and complicated driving principle of the mass body. It requires in fact a special compressed air generator which produces cyclic air pressure peaks, and an auxiliary reservoir at the downstream end of the blowgun to act as a pneumatic restoring spring. Transmission of energy from the compressed air generator to the mass body via the compressible, that is to say elastic, air requires a relatively long movement stroke of the mass body in order to accelerate the latter to the required speed. However, the long stroke entails a heavy frictional loss, which consumes part of the energy. The frictional loss is also increased by the fact that the mass body must lie, after the style of a piston, as closely as possible against the inside wall of the blowgun. Otherwise, compressed air will pass by the mass body and fill the auxiliary reservoir, which then counteracts too forcibly as a brake on the acceleration of the mass body. The fit of the mass body in the blowgun is in addition dependent on temperature, so that during operation the efficiency of the drive varies.

From DE-AS 27 24 324 a device for crushing bladder stones is known, which comprises a bundle of shock wires. In this case an electromagnetic drive is provided for each wire, an iron armature being made fast to the end of the wire and being driven by a stationary coil. A drive of this kind cannot generate an adequately effective shock wave, but on the contrary the shock wire is caused to make an oscillating movement over its whole length, the amplitude of the stroke being only very small and also resulting in only a low efficiency of the drive. Moreover, the mass of the iron armature is a hindrance.

The object of the invention is that of providing a device of the generic type which has a simpler and more practical drive.

This object is achieved by the characterizing features of claim 1.

The energy of an electrical energy pulse is transmitted directly to the mass body without the interposition of a transmission medium, such as air. Consequently, no restrictive conditions imposed by an intermediate carrier need be taken into account. The guide can have sufficient clearance to reduce frictional losses, and the energy is adequately developed over an acceptably short acceleration path. The pulse generator required is simple and inexpensive to produce.

Lithotrites are in practical use in which a shock wave is generated in the immediate vicinity of the stone by means of a spark discharge between two electrodes. For this purpose, a high-voltage pulse generator is necessary. The development according to claim 2 makes it possible in an advantageous manner to use alternatively a pulse generator of this kind, which already exists in most clinics, also with a device of the generic type. Accordingly, the transducer merely has to be designed and insulated in accordance with the high voltage which occurs.

A transducer according to the development according to claim 3 has the best controllability, but an electrostatic transducer is also possible.

The mass body can be subjected to the action of a magnetic field in various ways. Thus, it may be made of electrically conductive material, in which eddy currents setting up an opposing field are induced, whereby the mass body is shot out of the coil. If the mass body is made of permanent magnetic material, it can be actively moved in both directions of movement by a magnetic field reversing the direction. This of course requires careful matching of mass and frequency of the field oscillation to ensure that the mass body is not braked by the reversing magnetic field before it has transmitted its pulse to the impulse conducting wire.

The development according to claim 4 denotes a form of movement drive having very good controllability, and takes into account the fact that, irrespective of the polarity of the magnetic field, the mass body is always actively driven in one direction. This makes control simpler and is preferably suitable for single-pulse operation.

In conjunction with this development it is advantageous in accordance with claim 5 to return the mass body to the position of rest by means of a restoring spring, specifically in the form of an ordinary wire spring. Its behaviour can be most satisfactorily calculated and controlled in a practical manner.

In principle, the mass body can be mounted for swivelling similarly to a balance beam, the coil acting on one lever arm while the other lever arm strikes against the impulse conducting wire like a hammer of a hammer mechanism.

In contrast thereto, the development according to claim 6 relates to a linear movement of the mass body, whereby the energy is transmitted to the impulse conducting wire in the form of a more effective shock.

The development according to claim 7 is concerned particularly with the electromagnetic drive principle.

The extensions according to claims 8 and 9 bring about a reduction of the frictional resistance of the linear guide. The sliding coating is here provided on the stationary side, while the mass body can be left without a coating. This particularly takes into account the fact that exchangeable mass bodies of different masses are provided. Not being coated, they are less expensive.

A shock receiver according to claim 10 allows the mechanical strength of the shock introduction point to be better adapted to this type of load, whereas the impulse conducting wire can be made of a different material.

In the extension according to claim 11 the shock receiver serves as a stationary coupling for exchangeable impulse conducting wires, while its position relative to the mass body can be preset by design in a simple manner.

The development according to claim 12 provides a compact apparatus which can be easily handled.

Further advantageous developments and extensions of the invention will be seen in the following description of one exemplary embodiment, which is illustrated in the drawing, in which:

FIG. 1 is a schematic representation of a device according to the invention.

The device comprises, as its main components, a high-voltage pulse generator 11, an impulse generating device 12 and an impulse conducting wire 13. The latter can be made of a steel alloy and its constitution is similar to that of a piano string. This means that the material is so stiff that a mechanical shock introduced at one end is transmitted to the other end by molecular shocks in the interior of the wire. On the other hand, the material is sufficiently elastic to permit the bending of the impulse conducting wire to such an extent that, when introduced by means of an endoscope into a body, it can yield to the necessary deflections.

The pulse generator 11 is of the kind usually existing in clinics and is arranged to generate high-voltage pulses of variable amplitude and frequency. Consequently, a voltage controller 14, a storage capacitor 15 and a triggerable spark gap 16, which acts as a switch, are simply indicated schematically. A flexible cable 18 is connected to the terminals 17 and its other end is connected to a coil 19.

The coil 19 is wound coaxially to a geometrical longitudinal axis 21 and its cylindrical inner layer surrounds a tube 22 which is coaxial to it and which preferably consists of a plastics material having good sliding properties or is coated on its inside wall with a sliding coating. A casing 23 of soft iron has a stepped bore which is coaxial to the geometrical longitudinal axis 21 and comprises a first part 24 of the bore, in which the coil 19 is housed, and an axially adjoining second part 25 of the bore of smaller diameter, in which a rod-shaped shock receiver 26 of mechanically resistant material is held under elastic damping by means of a mounting 27 of plastics material. One end of the impulse conducting wire 13 is fastened rigidly but preferably detachably (for example by a screw connection) to the shock receiver 26. As shown in FIG. 1, the right-hand end face of the coil 19 is supported against the step 28 of the stepped bore. Its left-hand end face is held by a closure plate 29, which is also centered in the first part 24 of the bore and is secured in this axial position by a mounting cap 31. The closure plate 29 is made of soft iron and has a central hole 32, whose diameter is only slightly larger than the inside diameter of the tube 22. A cylindrical mass body 33 of soft iron is slidably mounted in the tube 22. Its length is greater than its diameter and at least slightly longer than the coil 19. In the schematic drawing the part of the mass body 33 which projects beyond the closure plate 29 on the left is shown as being an extension of said body which is of the same material and has the same diameter. It is understood that this is not essential. It is important only that a support plate 35 is attached to the mass body 33 at an axial distance from the left-hand outside surface 34 of the closure plate 29, so that a restoring spring 36 can be supported between said support plate and the outside surface 34. Said spring pulls the mass body 33 a certain distance out of the coil 19 to the position of rest shown in the drawing. This distance is limited, with damping, by a stop 37 on the inner side of a closure wall 38 of the mounting cap 31.

The drawing does not separately show a development in which the stop is arranged for axial adjustment relative to the closure wall 38 in order to enable the stroke of the mass body 33 to be varied.

In the position of rest shown in the drawing the right-hand end face 39 is situated at a predetermined distance (corresponding to the stroke) in front of the left-hand end face 41 of the shock receiver 26. If a voltage pulse is now triggered by means of the spark gap 16, the coil 19 converts it into a magnetic field pulse, which in turn accelerates the mass body 33 in the direction of the shock receiver 26. During the continuously accelerated movement, the mass body 33 thereby accumulates kinetic energy which, on impact against the shock receiver 26, is then introduced abruptly into the end face 41 of the latter. This kinetic energy then passes through the shock receiver 26 in the form of a shock wave and thereupon through the impulse conducting wire 13, without the latter being itself actually moved, and then passes out at the end of the impulse conducting wire 13. This shock energy can then be conducted by direct contact, or via a vibration reflector, onto the stone which is to be destroyed.

Instead of the electromagnetic impulse generator illustated here, an electrohydraulic lithotrite can be connected without difficulty to the pulse generator 11. In practice, only the probe to be introduced into the body then has to be selected in accordance with requirements.

According to a practical embodiment, the coil 19 and the tube 22 have a length of 2 cm, and the mass body 33 has a diameter of 5 mm, with a stroke of 3 to 4 mm.

I claim:

1. Stone crushing device for medical purposes, comprising an impulse conducting wire a first end of which is configured to point towards a stone which is to be destroyed, and further comprising an impulse generating device in which a second end of the impulse conducting wire is held, said impulse generating device having a mass body arranged for movement along a guide, and a drive arrangement by which the mass body can be driven from a first position, which is spaced apart from the second end of the impulse conducting wire, towards the second end of the impulse conducting wire and back away from the latter, in order to introduce a kinetic shock impulse into the impulse conducting wire, characterized in that the drive arrangement comprises a transducer (19) for converting an electrical energy pulse directly into kinetic energy of the mass body (33) in the direction of the second end of the impulse conducting wire (13) by generating a magnetic field.

2. Device according to claim 1, characterized in that transducer (19) is configured to be connectable to an electric high-voltage pulse generator (11).

3. Device according to claim 1, characterized in that the transducer comprises a coil (19) arranged stationary in the impulse generating device (12).

4. Device according to claim 3, characterized in that the mass body (33) consists of soft iron.

5. Device according to claim 3, further comprising a restoring spring in the impulse generating device (36) arranged for moving the mass body (33) into a position of rest spaced apart from the second end of the impulse conducting wire (13) when the magnetic field of the coil (19) is removed.

6. Device according to claim 3, further comprising a cylindrical shock receiver (26) with which the second end of the impulse conducting wire (13) is firmly connected and which is elastically mounted in the impulse generating device (12) and against which the mass body (33) is guided to strike in order to introduce a shock impulse to said impulse conducting wire.

7. Device according to claim 6, further comprising a screw connection, with which the second end of the impulse conducting wire (13) is connected fast but detachably to the shock receiver (26).

8. Device according to claim 7, characterized in that the impulse generating device (12) comprises a hollow cylindrical casing (23) in which the coil (19), the mass body (33) and the shock receiver (26), as well as the second end of the impulse conducting wire (13) directly adjacent thereto, are arranged coaxially with respect to one another.

9. Device according to claim 1, characterized in that the guide is in the form of a cylindrical tube (22) and in that the mass body (33) is in the form of a cylinder which fits with slight clearance into said tube and whose length is greater than its diameter.

10. Device according to claim 9, characterized in that the tube (22) consists of non-magnetic material.

11. Device according to claim 9, characterized in that an inside wall of the tube (22) is covered with a sliding coating.

12. Device according to claim 9, characterized in that the tube (22) is made of a plastics material having properties of a sliding coating.

* * * * *